US00PP25029P3

(12) United States Plant Patent
Suphachadiwong

(10) Patent No.: US PP25,029 P3
(45) Date of Patent: Nov. 4, 2014

(54) *VANDA* PLANT NAMED 'SPCDW1103'

(50) Latin Name: ***Vanda* hybrid**
Varietal Denomination: SPCDW1103

(75) Inventor: Thumrong Suphachadiwong, Chonburi (TH)

(73) Assignee: Suphachatwong Innovation (TH)

( * ) Notice: Subject to any disclaimer, the term of this patent is extended or adjusted under 35 U.S.C. 154(b) by 198 days.

(21) Appl. No.: 13/573,350

(22) Filed: Sep. 10, 2012

(65) Prior Publication Data

US 2013/0067624 P1 Mar. 14, 2013

(30) Foreign Application Priority Data

Sep. 12, 2011 (QZ) ..... PBR 20112164

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Vanda* cultivar named 'SPCDW1103' is disclosed, characterized by petals and sepals colored white with light purple netting. The new variety is a *Vanda,* typically produced as an indoor ornamental plant.

1 Drawing Sheet

Latin name of the genus and species: *Vanda* hybrid.
Variety denomination: 'SPCDW1103'.

BACKGROUND OF THE INVENTION

This application relates to a new cultivar of *Vanda,* as described in EU application number 2011/2164, filed Sep. 12, 2011, grant pending, to which applicant claims priority. The new variety is the product of a planned breeding program. The new variety originated as a seedling from the crossing of the unpatented, proprietary seed parent *Vanda* 'G248815' with the unpatented, proprietary pollen parent referred to as *Vanda* 'CTRV1815'. The crossing was made by the inventor in his research greenhouse in Chonburi, Thailand in October of 1987.

The new variety was first selected by the inventor, Thumrong Suphachadiwong, a citizen of Thailand, in June 1993, in a research greenhouse belonging to the inventor in Chonburi, Thailand. After identifying the new variety as a potentially interesting selection, the inventor continued confidential testing and propagation of 'SPCDW1103', assessing stability of the unique characteristics of this variety.

Asexual reproduction of the new cultivar 'SPCDW1103' was first performed at a commercial laboratory belonging to the inventor in Chonburi, Thailand by tissue culture in March of 1998. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1103' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1103'. These characteristics in combination distinguish 'SPCDW1103' as a new and distinct *Vanda* cultivar:

1. Unique sepal and petal coloration of white with light purple netting.
2. Improved plant compatibility for commercial growing methods.

PARENT COMPARISON

Plants of the new cultivar 'SPCDW1103' are similar to the seed parent, *Vanda* 'G248815' in most horticultural characteristics. The new variety, however, produces flowers with a different color than the seed parent.

Plants of the new cultivar 'SPCDW1103' are similar to the pollen parent, *Vanda* 'CTRV1815' in most horticultural characteristics. The new variety, however, produces flowers more easily than the pollen parent.

COMMERCIAL COMPARISON

'SPCDW1103' is similar in most horticultural characteristics to the unpatented commercial variety *Vanda* 'Blue Magic' in most horticultural characteristics. The new variety, however, produces sepals and petals colored white with light purple netting, whereas 'Blue Magic' produces petals and sepals that are white with a thick, dark purple netting. Additionally, the new variety has a lip colored medium purple, whereas 'Blue Magic' has a lip color of dark purple.

BRIEF DESCRIPTION OF THE PHOTOGRAPH

The accompanying photograph in FIG. 1 illustrates in full color a typical plant of 'SPCDW1103' grown in a commercial greenhouse in Honselersdijk, the Netherlands. This plant is approximately 5.5 years old, shown planted in a 8 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SPCDW1103' plants grown in a greenhouse in Honselersdijk, the Netherlands. Temperatures ranged were approximately 23° C. during the day and 19° C. at night. No photoperiodic or chemical treatments were given to the plants. When natural lighting fell below 150 Watt, artificial lighting is given at 10,000 lux for 16 hours a day. Measurements and numerical values represent averages of typical plant types.

Botanical classification: *Vanda* hybrid 'SPCDW1103'.

PROPAGATION

Type of propagation typically used: Tissue culture.

Propagation details: The time needed from for the start of a mericlone to get the small plants ready for deflasking is approximately 24 months under a controlled temperature of about 26 degrees Celsius. After that period plants have matured roots. Plants start to make roots in the last 6 months in flasks. After deflasking they remain in a shaded and controlled environment.

Root description: Moderately to heavy rooting with aerial roots only. Roots are very fleshy, non-fibrous.

- *Average length of mature roots.*—34.4 cm.
- *Average diameter of mature roots.*—3 mm.
- *Old roots colored yellow-green.*—Yellow-Green near RHS 146B and 146C.
- *Young roots colored greyed-green.*—Greyed-Green near RHS 196D.

PLANT

Growth habit: Monopodial, upright.

Height from soil line to top of foliage: Average height from base (plant grown in hanging basket, so no soil line present) to top of foliage: 33.7 cm.

Height from soil line to top of flowers: Average height from base (plant grown in hanging basket, so no soil line present) to top of flowers: 50.5 cm.

Plant spread: Average: 53.0 cm.

Normal pot size: Hanging basket (8×8 cm square).

Growth rate: Moderate.

Number of leaves per plant: Average: 22.

FOLIAGE

Leaf:

- *Arrangement.*—Distichous.
- *Average length.*—Approximately 23.6 cm.
- *Average width.*—Approximately 3.2 cm.
- *Shape of blade.*—Ligulate, carinate, slightly twisted lengthways.
- *Aspect.*—Very slightly curved.
- *Apex.*—Unequal emarginated to unequal praemorse.
- *Base.*—Sheathing. Sheath length: Average 2.3 cm. Sheath width: Average 2.2 cm. Sheath color: Yellow-green; near 144A.
- *Margin.*—Entire.
- *Texture of top surface.*—Smooth, dull.
- *Texture of bottom surface.*—Smooth, dull.
- *Color.*—Young foliage upper side: Green to yellow-green; a color in between 143A and 146A. Young foliage under side: Green; near 143C. Mature foliage upper side: Green; near 137B. Mature foliage under side: Yellow-green; near 144A.
- *Venation.*—Type: Parallel. Venation coloration: Green; near RHS N137B.

Petiole: No petioles present, leaves sessile.

FLOWERING CHARACTERISTICS

Flower bud: No flower buds observed at the time of the description.

Peduncle:

- *Length.*—Approximately 36.2 cm.
- *Width.*—Approximately 0.5 cm.
- *Aspect.*—Approximately 55° angle to rosette.
- *Strength.*—Strong.
- *Texture.*—Smooth, moderately glossy.
- *Color.*—Yellow-green; near RHS 144A.

INFLORESCENCE

Flowers per stem: Average: 7.

Inflorescence arrangement: Axially placed raceme.

Inflorescence height: Approximately 24.7 cm (measured from base of lowest flower to top of upper flower).

Inflorescence width: Approximately 19.3 cm.

INDIVIDUAL FLOWERS

Flower type: Zygomorphic (orchidaceous), typical shape for the genus *Vanda*.

- *Shape.*—Zygomorphic, consisting of three sepals and three petals, one of which is transformed into a labellum (lip).
- *Length (height).*—Approximately 11.3 cm.
- *Width.*—Approximately 9.2 cm.
- *Depth.*—Approximately 3.9 cm.
- *Fragrance.*—No fragrance.
- *Persistent.*—No.
- *Quantity of petals.*—3 (2 "traditional" petals and a labellum (lip), described separately).

Petals:

- *Arrangement.*—One lateral petal on each side.
- *Length.*—Approximately 5.5 cm.
- *Width.*—Approximately 4.0 cm.
- *Shape.*—Ovate to broad ovate.
- *Apex.*—Obtuse.
- *Base.*—Cuneate.
- *Margin.*—Entire, wavy.
- *Texture.*—Upper forward surface: Smooth, dull, velvety.
- *Texture.*—Lower back surface: Smooth, dull, velvety.
- *Color.*—When opening, forward surface: White; near RHS NN155C. When opening, back surface: White; near RHS NN155C. Fully Opened, forward surface: White; near RHS NN155D. Fully Opened, back surface: White; near RHS NN155D. Fading, forward surface: Not fading. Fading, back surface: Not fading.

*Color venation fully opened, forward surface.*—Violet; near RHS 85C.

*Color venation fully opened, back surface.*—Violet; near RHS 85C.

Labellum/lip:

*Shape.*—Three-lobed, lateral lobes involute, central lobe bi-lobed, with revolute margins.

*Length.*—Approximately 2.1 cm.

*Width.*—Approximately 1.4 cm.

*Texture.*—Smooth, dull, with 3 callosities.

*Tip.*—Bi-lobed.

*Base.*—Cuneate.

*Color.*—When opening, forward surface: lateral lobes white; near RHS NN155D, small central blotch yellow to yellow-orange; near RHS 13A and 14B; central lobe purple-violet; near RHS N82C, tip darker; near RHS N82B and 83D, callosities lighter; near RHS N82D. When opening, back surface: lateral lobes white; near RHS NN155C, central lobe near RHS N155A and NN155D, tip violet; near RHS N87C. Fully Opened, forward surface: lateral lobes white; near RHS-NN155D, small central blotch yellow to yellow-orange; near RHS-CC 13A and 14B; central lobe purple-violet; near RHS to N82C, tip darker; near RHS 83C, callosities lighter; near RHS N82D. Fully Opened, back surface: lateral lobes white; near RHS NN155C, central lobe near RHS NN155D, tip violet; near N87C. Fading, forward surface: Not fading. Fading, back surface: Not fading. Color Venation Fully Opened, forward surface: No venation visible on labellum. Color Venation Fully Opened, back surface: No venation visible on labellum.

*Margin.*—Entire.

Spurs:

*Quantity.*—Average: 1.

*Length.*—Approximately 0.9 cm.

*Width.*—Approximately 0.3 cm.

*Height.*—Approximately 0.6 cm.

*Shape.*—Short triangular, in line with central lobe of labellum.

*Apex.*—Obtuse.

*Base.*—Broad cuneate.

*Margin.*—Entire.

*Texture.*—Smooth, slightly glossy.

*Color.*—Violet to white; a color between RHS 85D and N155A.

Sepals:

*Quantity.*—Average: 3.

*Appearance.*—One dorsal sepal (pointing upright) and two lateral sepals.

*Length.*—Dorsal sepal approximately 5.9 cm. Lateral sepals approximately 5.6 cm.

*Width.*—Dorsal sepal approximately 3.9 cm. Lateral sepals approximately 5.0 cm.

*Shape.*—Broad ovate.

*Apex.*—Obtuse.

*Base.*—Cuneate.

*Margin.*—Entire, wavy.

*Texture.*—Smooth, dull.

*Color.*—White; near RHS NN155D, veined violet; near RHS 85C.

Pedicels:

*Length.*—Approximately 6.9 cm.

*Diameter.*—Approximately 0.4 cm.

*Angle.*—Approximately 50° angle to peduncle.

*Strength.*—Very strong.

*Texture.*—Smooth, axially angled with 5 "ribs", axially twisted (due to resupination), glossy.

*Color.*—White; near RHS NN155D, yellow-green towards the base; near RHS 145A.

REPRODUCTIVE ORGANS

Stamens, style and stigma fused into column? Yes.

Column length: Approximately 0.6 cm.

Column diameter: Approximately 0.7 cm.

Column color: White; near RHS NN155C.

Ovary:

*Position.*—Inferior.

*Diameter.*—Approximately 0.4 cm.

*Color.*—White; near RHS NN155C.

Pollinia color: Yellow to yellow-orange; 13A and 14B.

OTHER CHARACTERISTICS

Disease resistance: Good resistance to the normal diseases found in *Vanda.*

Drought tolerance and cold tolerance: Normal for species.

Fruit/seed production: No fruits/seeds detected to date.

What is claimed is:

1. A new and distinct cultivar of *Vanda* plant named 'SPCDW1103' as herein illustrated and described.

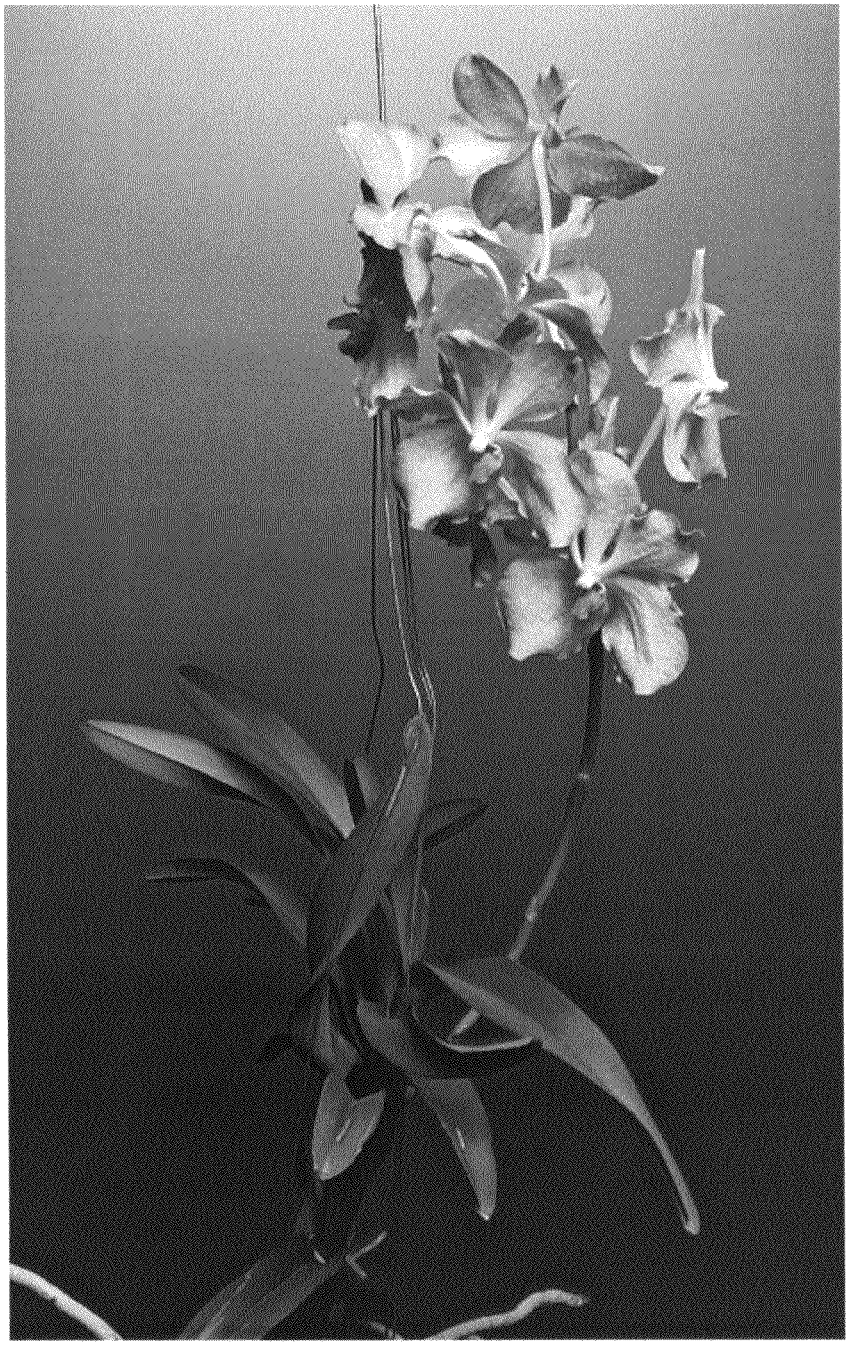

* * * * *